US00PP27548P3

(12) United States Plant Patent
Uchneat

(10) Patent No.: US PP27,548 P3
(45) Date of Patent: Jan. 17, 2017

(54) ***DIERVILLA* PLANT NAMED 'G2X88544'**

(50) Latin Name: *Diervilla×splendens*
Varietal Denomination: G2X88544

(71) Applicant: Michael S. Uchneat, Bellefonte, PA (US)

(72) Inventor: Michael S. Uchneat, Bellefonte, PA (US)

(73) Assignee: GardenGenetics LLC, Bellefonte, PA (US)

( * ) Notice: Subject to any disclaimer, the term of this patent is extended or adjusted under 35 U.S.C. 154(b) by 66 days.

(21) Appl. No.: 14/545,152

(22) Filed: Mar. 31, 2015

(65) Prior Publication Data

US 2016/0295762 P1 Oct. 6, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Diervilla* plant named 'G2X88544', characterized by its upright and outwardly spreading plant habit; vigorous growth habit; moderate to rapid growth rate; freely branching habit; dense and bushy appearance; developing leaves are orange in color; fully expanded leaves become golden orange in color in the autumn; and good garden performance.

2 Drawing Sheets

Botanical designation: *Diervilla×splendens*.
Cultivar denomination: 'G2X88544'.

BACKGROUND OF THE INVENTION

The present invention relates to a new and distinct cultivar of *Diervilla* plant, botanically known as *Diervilla×splendens*, commonly referred to as bush honeysuckle and hereinafter referred to by the cultivar name 'G2X88544'.

The new *Diervilla* is a product of a planned breeding program conducted by the Inventor in Bellefonte, Pa. The objective of the breeding program was to develop new compact and freely branching *Diervilla* plants with attractive leaf color.

The new *Diervilla* plant originated from an open-pollination in August, 2009 of a proprietary seedling selection of *Diervilla×splendens* identified as code number 3349-4, not patented, as the female, or seed, parent with an unknown proprietary selection of *Diervilla×splendens*. The new *Diervilla* plant was discovered and selected by the Inventor on Sep. 1, 2011 as a single flowering plant within the progeny of the stated open-pollination in a controlled environment in Bellefonte, Pa.

Asexual reproduction of the new *Diervilla* plant by vegetative cuttings in a controlled greenhouse environment in Bellefonte, Pa. has shown that the unique features of this new *Diervilla* plant are stable and reproduced true to type in successive generations of asexual reproduction.

SUMMARY OF THE INVENTION

Plants of the new *Diervilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'G2X88544'. These characteristics in combination distinguish 'G2X88544' as a new and distinct *Diervilla* plant:

1. Upright and outwardly spreading plant habit.
2. Vigorous growth habit and moderate to rapid growth rate.
3. Freely branching habit; dense and bushy appearance.
4. Developing leaves are orange in color.
5. Fully expanded leaves become golden orange in color in the autumn.
6. Good garden performance.

Plants of the new *Diervilla* can be compared to plants of the female parent selection. In side-by-side comparisons, plants of the new *Diervilla* differ primarily from plants of the female parent selection in leaf color as developing leaves of the female parent selection are green in color. In addition, developed leaves of the female parent selection. do not turn golden orange in the autumn.

Plants of the new *Diervilla* can be compared to plants of other selections of *Diervilla×splendens* known to the Inventor, not patented. In side-by-side comparisons, plants of the new *Diervilla* differed primarily from plants of other selections of *Diervilla×splendens* known to the Inventor in the following characteristics:

1. Plants of the new *Diervilla* were more freely branching and denser than plants of other selections of *Diervilla× splendens* known to the Inventor.
2. Plants of the new *Diervilla* and other selections of *Diervilla×splendens* known to the Inventor differed in developing leaf color as developing leaves of other selections of *Diervilla×splendens* were green in color.
3. Plants of the new *Diervilla* and other selections of *Diervilla×splendens* known to the Inventor differed in autumn leaf color as fully expanded leaves of other selections of *Diervilla×splendens* did not become golden orange in the autumn.

BRIEF DESCRIPTION OF THE PHOTOGRAPHS

The accompanying colored photographs illustrate the overall appearance of the new *Diervilla* plant showing the colors as true as it is reasonably possible to obtain in colored reproductions of this type. Colors in the photographs may differ slightly from the color values cited in the detailed botanical description which accurately describe the colors of the new *Diervilla* plant.

The photograph on the first sheet is a close-up view of a typical flowering plant of 'G2X88544' grown during the spring.

The photograph on the second sheet is a close-up view of a typical plant of 'G2X88544' grown during the autumn.

DETAILED BOTANICAL DESCRIPTION

The aforementioned photographs and following observations, measurements and values describe plants grown in the early summer in three-gallon containers in a polypropylene-covered shadehouse in Grand Haven, Mich. and under cultural practices typical of commercial *Diervilla* production. During the production of the plants, day temperatures ranged from 18° C. to 27° C. and night temperatures ranged from 5° C. to 10° C. Plants were two years old when the photographs and the description were taken. In the description, color references are made to The Royal Horticultural Society Colour Chart, 1995 Edition, except where general terms of ordinary dictionary significance are used.

Botanical classification: *Diervilla×splendens* 'G2X88544'.

Parentage:

*Female, or seed, parent*.—Proprietary seedling selection of *Diervilla×splendens* identified as code number 3349-4, not patented.

*Male, or pollen, parent*.—Unknown proprietary selection of *Diervilla×splendens*, not patented.

Propagation:

*Type*.—By vegetative cuttings.

*Time to initiate roots, summer*.—About 10 to 21 days at temperatures about 26° C.

*Time to initiate roots, winter*.—About two to three weeks at temperatures about 26° C.

*Time to produce a rooted young plant, summer*.—About four weeks at temperatures about 23° C.

*Time to produce a rooted young plant, winter*.—About four to five weeks at temperatures about 19° C.

*Root description*.—Medium to thick; whitish in color.

*Rooting habit*.—Moderate branching; medium density.

Plant description:

*Plant form and growth habit*.—Perennial deciduous shrub; upright and outwardly spreading plant habit, mounding; vigorous growth habit and moderate to rapid growth rate.

*Branching habit*.—Freely branching habit; about 80 to 100 lateral branches develop per plant; pinching enhances lateral branch development.

*Plant height*.—About 68 cm.

*Plant diameter* (*area of spread*).—About 98 cm.

Lateral branch description:

*Length*.—About 61 cm.

*Diameter*.—About 3.5 mm.

*Internode length*.—About 3.5 cm to 5 cm.

*Aspect*.—Erect to about 45° from vertical.

*Strength*.—Strong.

*Texture*.—Smooth, glabrous.

*Color, upper surface*.—Close to 144B.

*Color, lower surface*.—Close to 178A.

Leaf description:

*Arrangement*.—Opposite, simple.

*Length*.—About 6.5 cm to 13 cm.

*Width*.—About 2 cm to 5 cm.

*Shape*.—Lanceolate to ovate.

*Apex*.—Acuminate.

*Base*.—Obtuse.

*Margin*.—Serrulate.

*Texture, upper and lower surfaces*.—Smooth, glabrous.

*Venation pattern*.—Pinnate.

*Color*.—Developing leaves, upper surface: Close to 137A overlain with a blend close to 182A and 171A. Developing and fully expanded leaves, lower surface: Close to 137C overlain with close to 171C. Fully expanded leaves, upper surface: Close to 137A; venation, close to 145A; in the autumn, color becomes closer to 14A overlain with a blend close to 33A and 169A. Fully expanded leaves, lower surface: Close to 137C; venation, close to 145C; in the autumn, color becomes closer to 168C overlain with close to 14D.

*Petioles*.—Length: About 3 mm. Diameter: About 3 mm. Texture, upper and lower surfaces: Smooth, glabrous. Color, upper and lower surfaces: Close to 144B slightly overlain with close to 178A.

Flower description:

*Flower appearance and arrangement*.—Salverform flowers arranged in terminal cymes; freely flowering habit with about 18 to 33 flowers developing per inflorescence; flowers face upright to outwardly.

*Fragrance*.—None detected.

*Natural flowering season*.—Plants flower continuously during the spring to mid-summer in Michigan; flowers not persistent.

*Inflorescence height*.—About 4 cm.

*Inflorescence diameter*.—About 5 cm.

*Flower diameter*.—About 1.5 cm.

*Flower length*.—About 1.4 cm.

*Flower throat diameter* (*at base of petal lobes*).—About 5 mm.

*Flower tube length*.—About 7 mm.

*Flower tube diameter* (*at base of tube*).—About 2 mm.

*Flower buds*.—Length: About 1 cm. Diameter: About 2 mm. Shape: Oblong. Color: Close to 145A.

*Petals*.—Quantity and arrangement: Five fused with apices free. Length: About 8 mm. Width: About 3 mm. Shape: Narrowly oblong. Apex: Obtuse. Margin: Entire. Texture, upper and lower surfaces: Smooth, glabrous. Color: When opening and fully opened, upper surface: Close to 151D; flower throat, close to 151D. When opening and fully opened, lower surface: Close to 14A; flower tube, close to 14A.

*Sepals*.—Quantity and arrangement: Five in a single whorl. Length: About 2 mm. Width: About 0.5 mm to 1 mm. Shape: Lanceolate. Apex: Acuminate. Margin: Entire. Texture, upper and lower surfaces: Smooth, glabrous. Color, upper and lower surfaces: Close to 144B.

*Peduncles*.—Length: About 3 mm. Diameter: About 1 mm. Aspect: Erect to about 45° from vertical. Strength: Strong. Texture: Smooth, glabrous. Color: Close to 144B.

*Pedicels*.—Length: About 8 mm. Diameter: About 1 mm. Aspect: About 25° from peduncle axis. Strength: Strong. Texture: Smooth, glabrous. Color: Close to 144B.

*Reproductive organs*.—Stamens: Quantity per flower: Five. Filament length: About 5 mm. Filament color: Close to 145D. Anther length: About 3 mm. Anther shape: Lanceolate. Anther color: Close to 17A. Pollen amount: Scarce. Pollen color: Close to 17A. Pistils: Quantity per flower: One. Pistil length: About 1.4 cm. Stigma shape: Round. Stigma color: Close to 144B. Style length: About 1.4 cm. Style color: Close to 144B. Ovary color: Close to 144B.

*Fruits and seeds*.—Fruit and seed development have not been observed on plants of the new *Diervilla.*

Garden performance: Plants of the new *Diervilla* have been observed to have good garden performance and to tolerate rain, wind and temperatures ranging from −28° C. to 35° C.

Pathogen & pest resistance: Plants of the new *Diervilla* have not been shown to be resistant to pathogens and pests common to *Diervilla* plants.

It is claimed:

1. A new and distinct *Diervilla* plant named 'G2X88544' as illustrated and described.

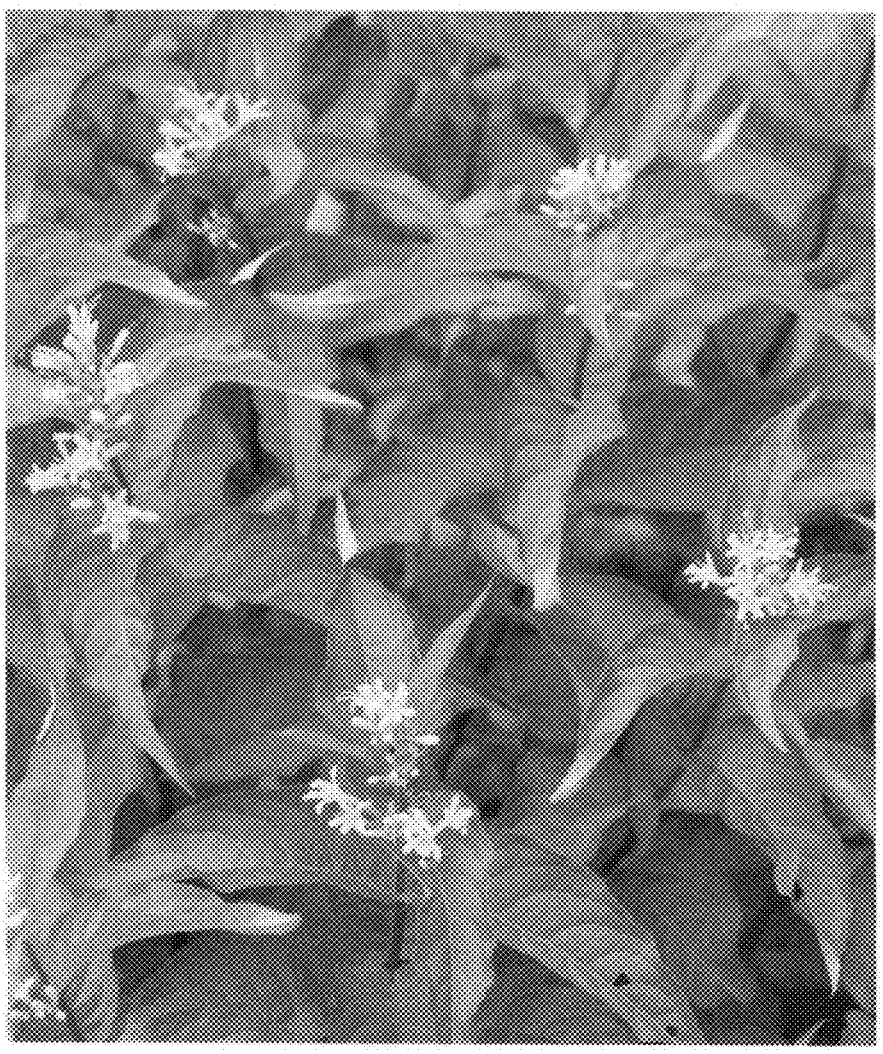

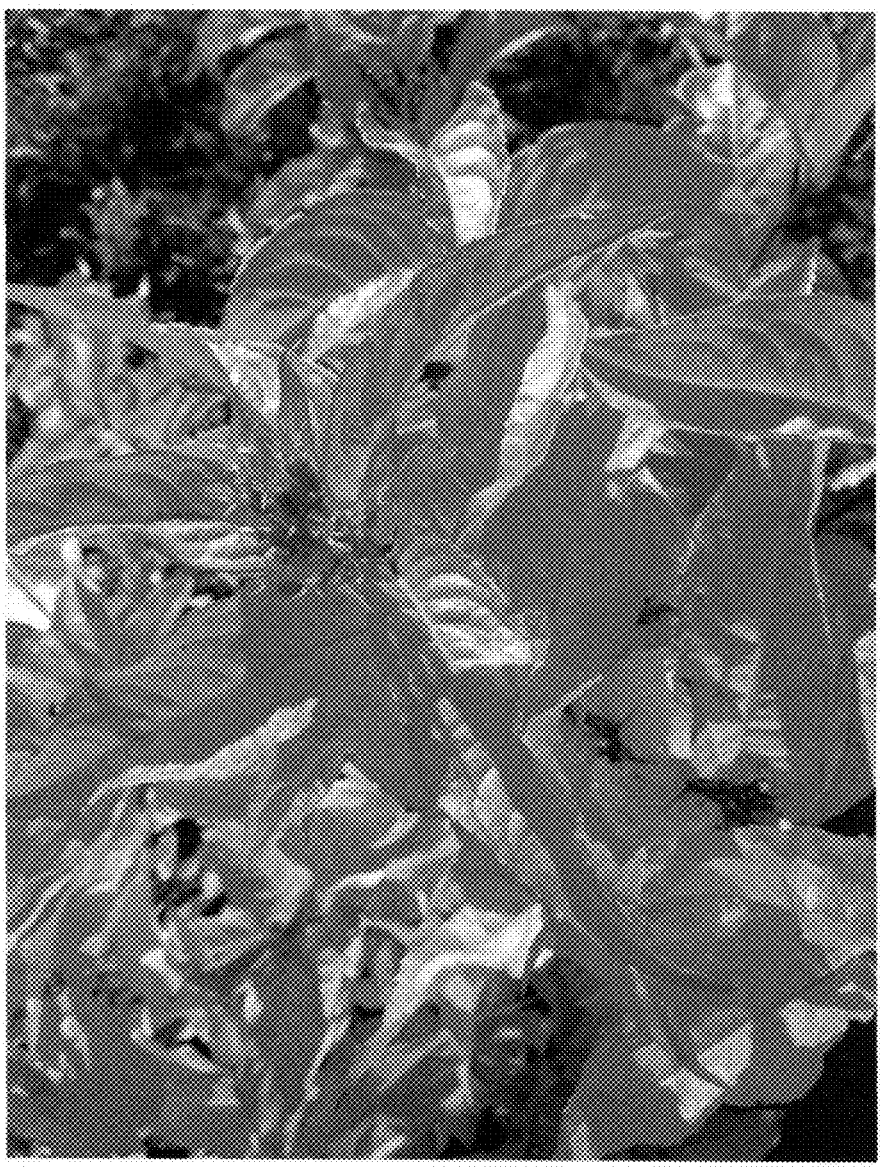

* * * * *